(12) United States Patent
Yudkovitch et al.

(10) Patent No.: US 7,672,849 B2
(45) Date of Patent: Mar. 2, 2010

(54) SYSTEMS AND METHODS FOR VOICE CONTROL OF A MEDICAL IMAGING DEVICE

(75) Inventors: Laurence M. Yudkovitch, Milwaukee, WI (US); Farshid Farrokhnia, Brookfield, WI (US); Richard Chiao, Menomonee Falls, WI (US)

(73) Assignee: GE Medical Systems Global Technology Company LLC, Waukesha, WI (US)

( * ) Notice: Subject to any disclaimer, the term of this patent is extended or adjusted under 35 U.S.C. 154(b) by 311 days.

(21) Appl. No.: 11/761,488

(22) Filed: Jun. 12, 2007

(65) Prior Publication Data
US 2007/0233499 A1    Oct. 4, 2007

Related U.S. Application Data

(63) Continuation of application No. 10/744,511, filed on Dec. 23, 2003, now Pat. No. 7,247,139.

(60) Provisional application No. 60/501,471, filed on Sep. 9, 2003.

(51) Int. Cl.
*G10L 21/00* (2006.01)
(52) U.S. Cl. ........................ 704/270; 704/275
(58) Field of Classification Search ........................ None
See application file for complete search history.

(56) References Cited

U.S. PATENT DOCUMENTS

| | | | | |
|---|---|---|---|---|
| 5,345,538 A * | 9/1994 | Narayannan et al. | ........ | 704/275 |
| 5,544,654 A * | 8/1996 | Murphy et al. | ............... | 600/443 |
| 6,224,542 B1 * | 5/2001 | Chang et al. | ................. | 600/109 |
| 6,278,975 B1 * | 8/2001 | Brant et al. | .................. | 704/275 |
| 6,591,239 B1 * | 7/2003 | McCall et al. | ............... | 704/275 |
| 6,743,175 B2 * | 6/2004 | Greenberg | ................... | 600/437 |
| 6,968,223 B2 | 11/2005 | Hanover | | |
| 7,027,991 B2 * | 4/2006 | Alexander et al. | ........... | 704/275 |
| 7,127,401 B2 * | 10/2006 | Miller | ......................... | 704/275 |
| 7,286,992 B2 * | 10/2007 | Sander et al. | ................ | 704/275 |
| 2003/0068011 A1 * | 4/2003 | Johnson et al. | .............. | 378/115 |

* cited by examiner

*Primary Examiner*—David R Hudspeth
*Assistant Examiner*—Brian L Albertalli
(74) *Attorney, Agent, or Firm*—McAndrews, Held & Malloy, Ltd.; Peter J. Vogel; Michael A. Dellapenna (57) ABSTRACT

The present invention relates to a method and apparatus for providing voice control of a device, an ultrasound device for example. One embodiment of the present invention comprises an apparatus for providing voice control of the ultrasound device having a plurality of features. The apparatus comprises a memory device adapted to store a plurality of voice commands for controlling the ultrasound device, where the plurality of voice commands has at least two different voice commands that active a single feature of the ultrasound device; a selection module adapted to selecting at least one of the at least two different voice commands; and a translator module adapted to derive a signal from the selected voice command and transmit it to the ultrasound device.

18 Claims, 5 Drawing Sheets

SYSTEMS AND METHODS FOR VOICE CONTROL OF A MEDICAL IMAGING DEVICE

RELATED APPLICATIONS

This application is a continuation of U.S. application Ser. No. 10/744,511, filed Dec. 23, 2003, which is related to, and claims benefit of and priority from, U.S. Provisional Application No. 60/501,471, filed on Sep. 9, 2003, titled "Method and Apparatus for Natural Voice Control of an Ultrasound Machine." The foregoing applications are herein incorporated by reference in their entirety.

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

This application is directed in general to control of medical ultrasound machines. This application is directed in particular to a voice control system adapted to provide speech recognition without compromising control of the ultrasound machine.

It is contemplated that a number of situations may exist where, when using an ultrasound machine, an operator (a doctor or sonographer for example) may have difficulty completing the exam using only the console. Some examples include upper and lower extremity exams, compression exams, carotid exams, neo-natal head exams, and portables. Working with large patients may further pose a problem to some smaller operators who can't physically reach both the console and the location they need to scan. In addition, use of manual controls may lead to a repetitive stress disorder, causing the operator discomfort and decreasing their productivity.

Alternate methods exist for controlling the ultrasound machine while away from the console (i.e., when the keyboard is insufficient or inconvenient). Some examples include using a remote wand, a footswitch, a second operator and limited voice control of the ultrasound machine.

A remote wand coupled to the ultrasound machine enables an operator to conduct difficult exams. However, the remote wand does not help the operator complete an exam requiring the use of both hands (while supporting a patient's leg for example). A foot-switch attached to the ultrasound machine enables the operator to depress a small number of keys (typically two) by operating the switches with his or her feet. The keys on the foot-switch may be defined by the operator to be the most critical functions that are necessary. This provides limited control of the ultrasound machine. The foot-switch solution is limited in several ways. Primarily, it cannot provide broad control of the ultrasound machine. Generally a foot-switch may only support up to three commands. The operator must select which functions are to be controlled by the foot-switch based on their immediate needs. This is insufficient for most exams.

It is contemplated that an additional operator or assistant may assist with the examination, controlling the keyboard of the ultrasound machine in response to the doctor or sonographer spoken commands who are actually conducting the examination. It should be appreciated that having an additional operator help with conducting an ultrasound examination may increase the cost of the examination. Further, there exists the possibility of miscommunication between the sonographer conducting the examination and the assistant.

It should be appreciated that one limitation associated with using voice commands to control an ultrasound device is communicating the command set to the user. Leading ultrasound systems have hundreds of available commands. Memorizing all the hundreds of commands is difficult. Such limitation, in conjunction with the variable accuracy in ultrasound systems, may lead to situations in which the user isn't sure if the lack of system response is due to an invalid command, or the system lack of understanding of the command.

A limited voice control system has been implemented which provides the operator with the ability to verbally depress some of the keys of the keyboard using spoken commands. This voice control system recognizes a limited vocabulary of spoken commands. This vocabulary enables the operator to send a subset of the commands that may also be sent by the keyboard.

Still another system for voice control of an ultrasound machine is disclosed in U.S. Pat. No. 5,544,654. This voice control system limits the number of commands available to the user at any time dependent on the state of the ultrasound system.

Thus there exists a need for natural voice control of a device (an ultrasound machine, apparatus or device for example).

BRIEF SUMMARY OF THE INVENTION

Embodiment of the present invention relates to natural voice commands used to simplify operations of a device (an ultrasound machine for example). More specifically, embodiments of the present invention comprise a system and method adapted to provide simple and efficient operation of a device (an ultrasound machine for example) using at least voice control. At least one embodiment of the ultrasound voice control system enables the user to complete an exam without using the console (i.e., the keyboard). This may be accomplished using a natural and flexible command grammar (i.e., structure) so that in general, the sonographer's first command controls the machine. Commands in the present invention are short and concise; using language that is relevant to the user; and map naturally into the verbal domain. While a console control may only enable toggling the current state of a feature, it is contemplated that voice control in accordance with one embodiment of the present invention will provide for choosing toggling, enabling or disabling the state.

In particular, one embodiment relates to a method for controlling a device using voice commands comprising a plurality of voice commands for controlling the device, where the plurality of voice commands has at least two different voice commands that activate a single feature of the device. At least one of the at least two different voice commands is selected and a signal is derived. The derived signal is applied to the device.

Embodiments of the present invention comprise using at least one qualitative, quantitative, or some combination of the two voice commands, where frequently used voice commands have a shorter word length than less frequently used voice commands. It is contemplated that quantitative voice commands may be adjusted, by applying an incremental value (a positive or negative value for example) thereto. Other embodiments comprise at least a first quantitative voice command associated with at least a second quantitative voice command. Still other embodiments comprise providing feedback (to a user or operator for example), translating one or more voice commands into a signal, and using non-voice commands (key strokes for example) in addition to voice commands to control or adjust the device.

Another embodiment relates to a method for controlling an ultrasound device using voice commands having a plurality of features. This method comprises providing a plurality of voice commands for controlling the device, the plurality of voice commands having at least two different voice commands that activate a single feature of the device. At least one of the two different voice commands is selected. The selected voice command is translated into a signal provided to the device.

Yet another embodiment of the present invention relates to a method for voice-control of an ultrasound system. In one embodiment, the method comprises receiving spoken quantitative and qualitative commands associated with one another, wherein a first qualitative command is spoken in conjunction with an associated first quantitative command, and controlling a feature of an ultrasound machine based on the first quantitative command. The method further comprises adjusting control of the feature based on the first qualitative command.

Still another embodiment relates to an apparatus for providing voice activation or control of an ultrasound device having a plurality of features. This apparatus comprises a memory device adapted to store a plurality of voice commands for controlling the ultrasound device, where the plurality of voice commands has at least two different voice commands that activate a single feature of the ultrasound device. The apparatus further comprises a selection module adapted to selecting at least one of the two different voice commands and a translator module adapted to derive a signal from the selected voice command and transmit it to the ultrasound device. At least one embodiment comprises adjusting the voice commands (i.e., adjusting at least one of the qualitative or quantitative voice commands), where adjusting the quantitative voice command comprises storing at least one qualitative voice command and applying an incremental value thereto.

Another embodiment of the present invention relates to a voice-controlled ultrasound system. In one embodiment, the ultrasound system comprises an ultrasound machine, an input and a controller. The ultrasound machine operates based on features. The input receives from a user spoken quantitative and qualitative commands associated with one another, wherein a first qualitative command is spoken in conjunction with an associated first quantitative command. The controller controls a feature of the ultrasound machine based on the first quantitative command, the controller adjusting control of the feature based on the first qualitative command. In at least one embodiment, the controller may apply a default direction or value for lacking direction or value. For example, if a first quantitative voice command includes at least a feature command and a relative value, but lacks a direction, the controller may apply a default direction. Likewise, if the first quantitative voice command includes at least a feature command and a direction, but lacks a relative value, the controller may apply a default relative value.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

For the purpose of illustration only, the following detailed description references a certain embodiment of an ultrasound machine, apparatus or device. However, it is understood that the present invention may be used with other devices or imaging systems.

Figure 1:
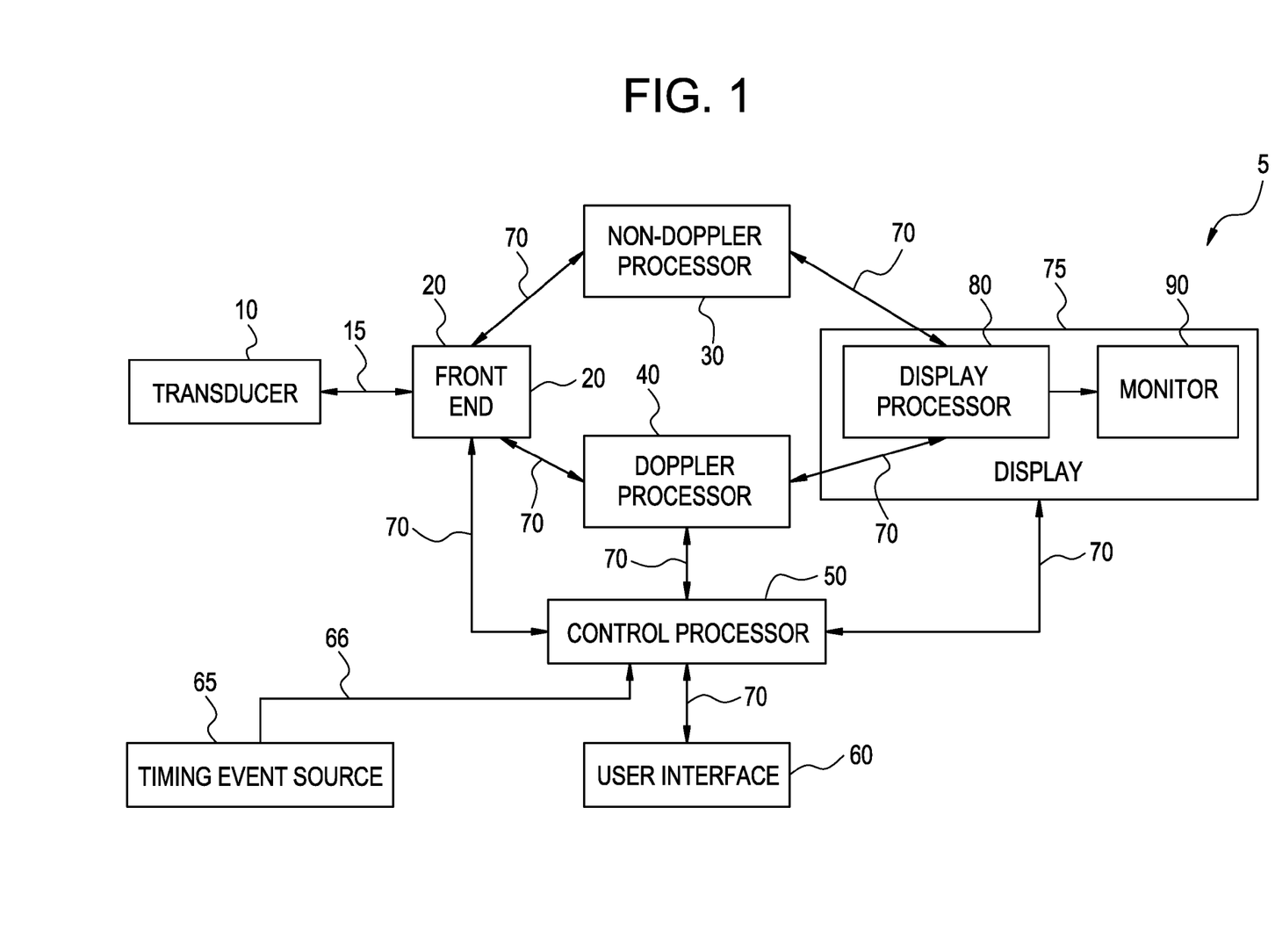
FIG. 1 illustrates a block diagram of an embodiment of an ultrasound machine made in accordance with certain embodiments of the present invention.

FIG. 1 illustrates an embodiment of an ultrasound machine, generally designated 5, in accordance with embodiments of the present invention. A transducer 10 transmits ultrasound waves into a subject (live tissue for example) by converting electrical analog signals to ultrasonic energy and receives the ultrasound waves backscattered from the subject by converting ultrasonic energy to analog electrical signals. A front-end 20, that in one embodiment comprises a receiver, transmitter, and beamformer, may be used to create the necessary transmitted waveforms, beam patterns, receiver filtering techniques, and demodulation schemes that are used for the various imaging modes. Front-end 20 performs such functions, converting digital data to analog data and vice versa. Front-end 20 interfaces to transducer 10 using analog interface 15 and interfaces to a non-Doppler processor 30, a Doppler processor 40 and a control processor 50 over a bus 70 (digital bus for example). Bus 70 may comprise several digital sub-buses, each sub-bus having its own unique configuration and providing digital data interfaces to various parts of the ultrasound machine 5.

Non-Doppler processor 30 is, in one embodiment, adapted to provide amplitude detection functions and data compression functions used for imaging modes such as B-mode, M-mode, and harmonic imaging. Doppler processor 40, in one embodiment provides clutter filtering functions and movement parameter estimation functions used for imaging modes such as tissue velocity imaging (TVI), strain rate imaging (SRI), and color M-mode. In one embodiment, the two processors, 30 and 40, accept digital signal data from the front-end 20, process the digital signal data into estimated parameter values, and pass the estimated parameter values to processor 50 and a display 75 over digital bus 70. The estimated parameter values may be created using the received signals in frequency bands centered at the fundamental, harmonics, or sub-harmonics of the transmitted signals in a manner known to those skilled in the art.

Display 75 is adapted, in one embodiment, to provide scan-conversion functions, color mapping functions, and tissue/flow arbitration functions, performed by a display processor 80 which accepts digital parameter values from processors 30, 40, and 50, processes, maps, and formats the digital data for display, converts the digital display data to analog display signals, and communicate the analog display signals to a monitor 90. Monitor 90 accepts the analog display signals from display processor 80 and displays the resultant image.

A user interface 60 enables user commands to be input by the operator to the ultrasound machine 5 through control processor 50. User interface 60 may comprise a keyboard, mouse, switches, knobs, buttons, track balls, foot pedals, a microphone for inputting voice commands and on-screen menus, among other devices.

A timing event source 65 generates a cardiac timing event signal 66 that represents the cardiac waveform of the subject. The timing event signal 66 is input to ultrasound machine 5 through control processor 50.

In one embodiment, control processor 50 comprises the main, central processor of the ultrasound machine 5, interfacing to various other parts of the ultrasound machine 5 through digital bus 70. Control processor 50 executes the various data algorithms and functions for the various imaging and diagnostic modes. Digital data and commands may be communicated between control processor 50 and other various parts of the ultrasound machine 5. As an alternative, the functions performed by control processor 50 may be performed by multiple processors, or may be integrated into processors 30, 40, or 80, or any combination thereof. As a further alternative, the functions of processors 30, 40, 50, and 80 may be integrated into a single PC backend.

Figure 2:
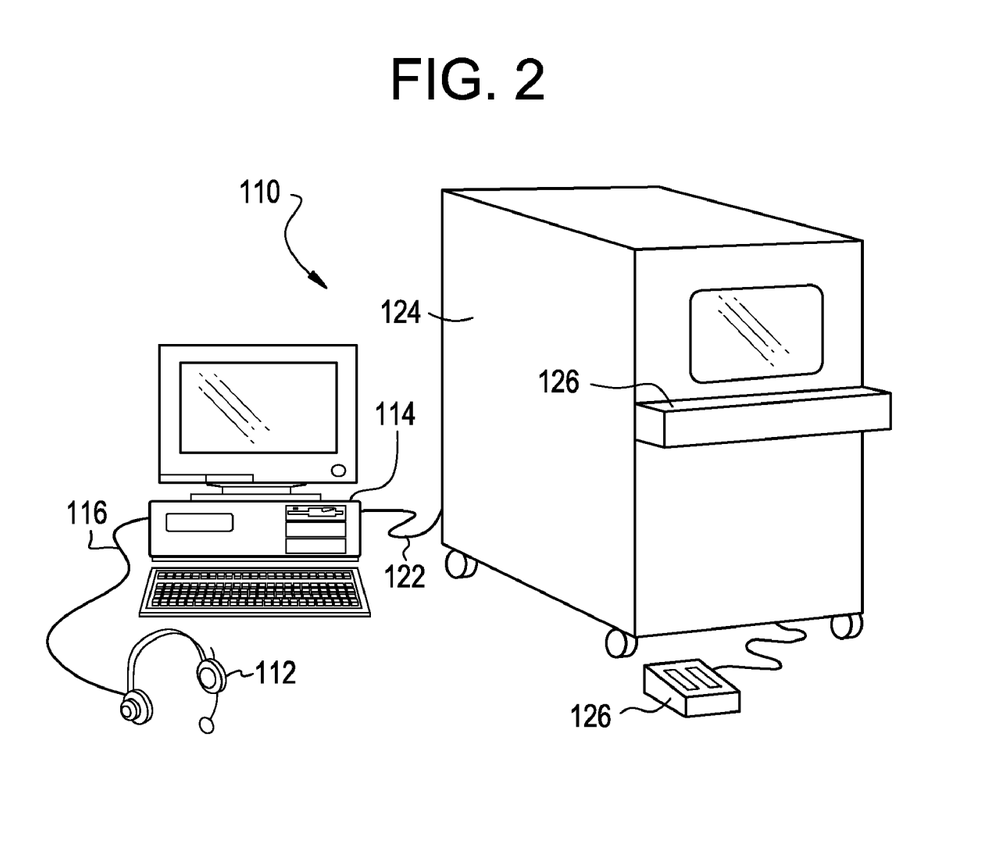
FIG. 2 illustrates a voice activation system for controlling an ultrasound machine in accordance with certain embodiments of the present invention.

In at least one embodiment, host computer or PC 114 contains at least one control processor 50 and hardware and software for providing voice control operation of an ultrasound system or machine. FIG. 2 illustrates an ultrasound machine, device or apparatus, generally designated 110, having a voice activation system, for controlling the ultrasound machine (similar to that provided previously) in accordance with certain embodiments of the present invention. In the illustrated embodiment, a microphone 112 is coupled to or communicates with a host computer 114 via connection 116. In at least one embodiment, host computer or PC 114 contains at least control processor 50 and hardware and software for providing operation of the ultrasound system using voice control.

In one embodiment, the microphone 112 is a headset microphone. However, any microphone suitable for speech recognition applications (including, for example, lapel microphones, hand-held microphones, stand-mounted microphones, "far-talk" microphones, etc.) may be used. Additionally any mounting option may be used. It is contemplated that connection 116 connects the microphone 112 to the speech recognition hardware. In the illustrated implementation, a wired connection is illustrated. However, any microphone connection may be used, including, for example, wireless connections.

Figure 3:
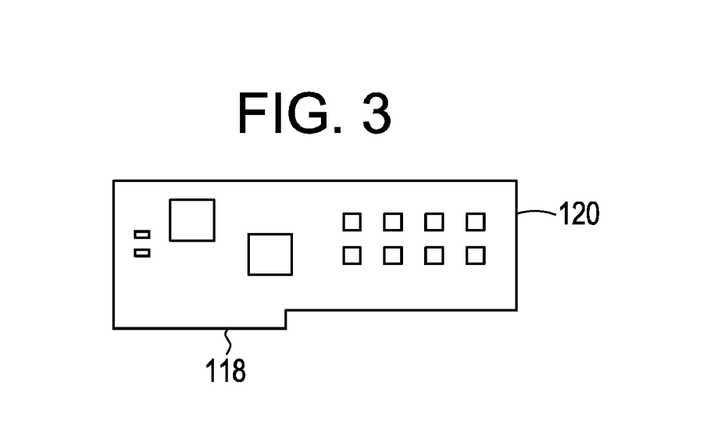
FIG. 3 illustrates an add-in card used with an ultrasound system or machine (similar to that illustrated in FIGS. 1 and 2) in accordance with certain embodiments of the present invention.

FIG. 3 illustrates connection 118 and speech recognition hardware/software 120 in accordance with one embodiment of the present invention. In this embodiment, connection 118 connects the speech recognition system to host computer 114.

In one embodiment, the speech recognition system is an add-in card, for example interfacing using an PCI bus for example. However, other embodiments are contemplated, wherein the speech recognition system may be a separate module connected via a serial interface, or it may be designed to interface to the bus of another type of host computer. This embodiment further contemplates speech recognition hardware/software 120 adapted to perform speech recognition. Any suitable commercial or custom speech recognition system may be used.

FIG. 2 further illustrates host computer 114 coupled to ultrasound system 124 via connection 122. In one embodiment, connection 122 comprises a wired connection, although other interfaces or connections are contemplated, including wireless connections. In one embodiment, the present invention comprises an embedded design, where the host computer is contained within the ultrasound system, connected to the computer bus of the ultrasound system for example. In this illustrated embodiment, the ultrasound system 124 includes a keyboard 126 and foot-switch 128.

Figure 4:
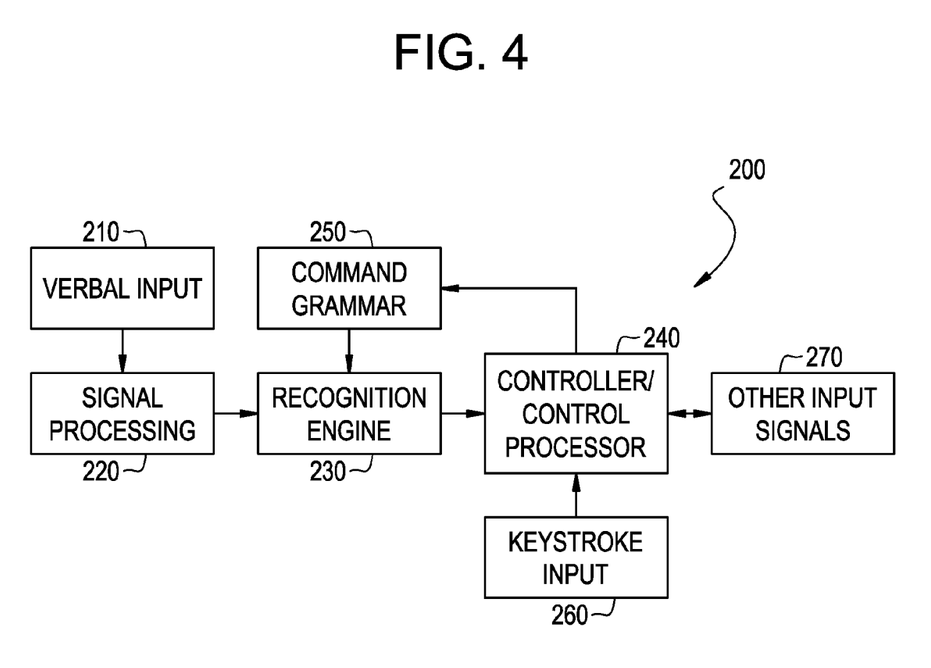
FIG. 4 illustrates a functional block diagram depicting the operation of a voice activation system in accordance with certain embodiments of the present invention.

FIG. 4 depicts a functional block diagram, generally designated 200, illustrating voice control of an ultrasound machine or device similar to that described previously in accordance with embodiments of the present invention. In one embodiment of the present invention, verbal input or voice commands 210 are entered into the system using a microphone. Any suitable microphone is contemplated. It is contemplated that microphone may be connected to the system or device using any suitable connection, including wireless connections.

FIG. 4 further depicts that that the verbal input 210 is translated or one or more signals derived from the verbal input (i.e., signal 1 processing 220). In one embodiment, this function may be implemented as part of the commercial speech recognition product.

Recognition engine 230 is shown communicating with signal processing 220 and command grammar 250. In one embodiment this function may be part of the speech recognition product, including hardware and software. Recognition engine 230 compares the incoming speech to the vocabulary or command grammar 250 to determine if the spoken word matches any of the defined commands.

FIG. 4 further illustrates command grammar 250 communicating with recognition engine 230 and controller/control processor 240. In one embodiment, the command grammar 250 contains the reference commands that may be issued by the user. In at least one embodiment, the total command grammar 250 may be subdivided into groups, or sub-vocabularies, each of which may be selected or deselected as part of the command grammar. It is contemplated that this function is also part of the speech recognition product, but may be customized to a particular application. The command structure and sub-vocabularies may be stored on disk or in the controller/control processor 240. Similar resources for the creation and management of vocabularies exist for the other commercial speech recognition products.

In at least one embodiment, the system or device includes an ultrasound system controller or control processor 240 (similar to that provided previously). In at least this embodiment, the controller/control processor 240 communicates with at least the recognition engine 230 and the command grammar 250 and is the software/hardware module that controls the overall ultrasound system or device.

It is further contemplated, that in addition to be controlled using verbal controls, at least one embodiment of the present invention may be controlled using keystroke inputs or other input signals 260 and 270 respectively. FIG. 4 contemplates that an ultrasound system keyboard and other input devices (mouse, rollerballs, footswitches, image-capture devices, touch panel, a wireless remote wand, other wireless devices, etc.) adapted to produce and transmit one or more inputs or signals to the controller/control processor 240.

Embodiments of the present invention comprise a system and method adapted to provide simple and efficient operation of a device (an ultrasound machine for example) using at least voice control. At least one embodiment of the ultrasound voice control system enables the user to complete an exam without using the console (i.e., the keyboard). This may be accomplished using a natural and flexible command grammar (i.e., structure) so that in general, the sonographer's first command controls the machine. Commands in the present invention are short and concise; using language that is relevant to the user; and map naturally into the verbal domain. While a console control may only enable toggling the current state of a feature, it is contemplated that voice control in accordance with one embodiment of the present invention will provide for choosing toggling, enabling or disabling the state.

For example, the console control for Doppler mode may simply be a toggle button. However, the voice commands associated with the Doppler mode may include "Doppler" (to toggle), "Doppler On" (to enable), and "Doppler off" (to disable). To be flexible and natural, embodiments of the present should also support "Turn on Doppler" and "Enable Doppler".

To increase accuracy for the speech engine, a command grammar is established so that different functions are activated by commands in a mutually exclusive language space. This means that commands have keywords that sound different. Additionally, in contrast to known systems, where the commands consist of single words, most commands have a minimum word length of two words. Exceptions include commands that are used very or more frequently (Freeze, Unfreeze, and Print for example) and very unique words (Harmonics, or Contrast that are multi-syllabic and not easily confused). Further, it should be appreciated that "gain up" and "gate up" would not be two permissible commands as 'gain' and 'gate' are easily mistaken. However, adding the word 'move' prior to saying 'gate' would be acceptable. Therefore, the commands may become "move gate up" or "gain up".

It is contemplated that, while many features of the ultrasound device may simply be enabled or disabled, other features (gain for example) are adjustable. That is, these features enable a user to select and or change a setting using a range of possible values (e.g. depth may range from 0 to 15). Voice control of these adjustable features may be accomplished by stating the command, a direction, and a value. Examples of such commands include changing gain (2D, color, Doppler, etc . . . ), depth, zoom, and baseline. Examples of direction may comprise positive and negative directions or values (and all synonyms). In one embodiment, if a direction is omitted, then a positive direction or value is assumed. The value represents a quantity to change the current value (or relative value for example) in the direction specified. If no value is specified, a default value (1 for example) is assumed, but a direction must be specified if no value is specified. It should also be appreciated that, while a default value of l is assumed, other default values may be used, including the same or differing default values selected or preset by the user. It should also be understood that while the example command provided below are in English, other languages are contemplated. Examples are provided in Table 1 below.

TABLE 1

| Spoken Command | Action |
| --- | --- |
| Gain Up | Increases the current gain by one (default value). So if the gain is currently at 6, it would become 7. |
| Increase gain | Increases the current gain by one (default value). Here the direction precedes the command. |
| Increase gain | Increases the current gain by one (default value). So if the gain is currently at 3, it would become 4. However, it is also contemplated that the next default value may be preset to two. |
| Gain up 5 | Increases the gain by 5. |
| Gain 5 | Increases the gain by 5. (Assumes positive direction by default) |
| Decrease gain 5 | Decreases the gain by 5. |
| Decrease gain by 5 | Decreases the gain by 5. |
| Gain minus 5 | Decreases the gain by 5. |
| B Flow Gain Up | Increases the B Mode gain by 1. |
| B Mode Gain Up | Increases the B Mode gain by 1. |
| B Gain Up | Increases the B Mode gain by 1. |
| B Gain Plus 1 | Increases the B Mode gain by 1. |

Although it is contemplated that values may be absolute numbers, these values are usually relative to the current value (i.e., alternatively referred to as a relative value, change value, or incremental value), and represent a similar quantity (or change) that may be realized from keyboard operation. In other words, changing a value by 1 is the same as flipping the keyboard switch once or rotating a dial one click. The positive direction normally refers to flipping a switch up, right or turning a rotary clockwise. Embodiments of the present invention may cover commands normally handled by moving a trackball or other positioning device, including positioning and sizing a region of interest ("ROI") or moving a cursor on a display screen. In this embodiment, it is contemplated that the direction must be specified as horizontal or vertical.

Once a quantitative command (such as those described previously) has been issued, the user frequently needs to make small adjustments. For example, gain is frequently adjusted a few times until the desired setting is reached. In one embodiment, one or more qualitative commands (an incremental value for example) may be used to make such adjustments. Embodiments of the system remember (i.e., store) the last quantitative command performed, applying the incremental value to it. In this embodiment, both a direction and value may be required. Examples are illustrated in Table 2 below.

TABLE 2

| Long Form | Short Form |
| --- | --- |
| Gain up 10 | Gain up 10 |
| Gain down 5 | Down 5 |
| Gain up 2 | Plus 2 |
| Gains down 1 | Minus 1 |

Still other embodiments comprise verbal commands specifically used to adjust gain. These commands may comprise gain values that specifically apply to different modes, such as 2D gain, color gain, Doppler gain, etc. The user may specifically state which gain is to be adjusted using the full name (i.e. B-Gain, Color gain, etc.). Otherwise, embodiments of the present invention will assume that the gain for the current active mode is to be adjusted if only the command "gain" is specified.

It should be appreciated that, one of the challenges associated with a voice-controlled system having many commands is learning to use the system. Different methods are available to assist the user. A sample script may be read, where different scripts may be used to cover different exam categories. The script will guide the user through a typical exam, covering most of the system features. Such scripts will demonstrate various methods for activating the commands and provide the user with real-time feedback regarding what the commands do. Another method comprises an interactive program that instructs the user in how to perform a specific task, verifying that they have completed it. Lastly, the user may use a quick-reference card that summarizes all of the commands. Such reference card will list only one or two forms of a command, usually the shortest form. These commands may be grouped by function so they may be easily identified.

While the user is using the system, embodiments may include tools that assist the user to access a function. For features normally accessed from the console, users may use a "How do I use?" command and then press the button. The system will verbally respond a method to activate the feature and/or display the grammar on screen. For other features that are activated by "soft keys" (a touch panel having varying options for example) the user may use a "How do I use xxx" command, where 'xxx' is a common name for the feature. If the system is unsure of the exact feature the user is referring to, it may prompt the user to clarify. This prompt may be provided verbally or displayed on-screen.

During normal usage, it is contemplated that the present invention provides feedback to the user regarding what has been done. For example, after issuing a voice command, the user may not be certain if the system heard the issued command and interpreted the command correctly. To satisfy this need, embodiments of the present invention may provide a non-verbal audio confirmation to the user when it hears a command (beeps/dings for example). Additionally, after a command is recognized, it may be displayed on a screen. This provides the user the opportunity to verify that the system heard the command (i.e., visual confirmation), or to determine what the system did in case the command was misunderstood.

Figure 5:
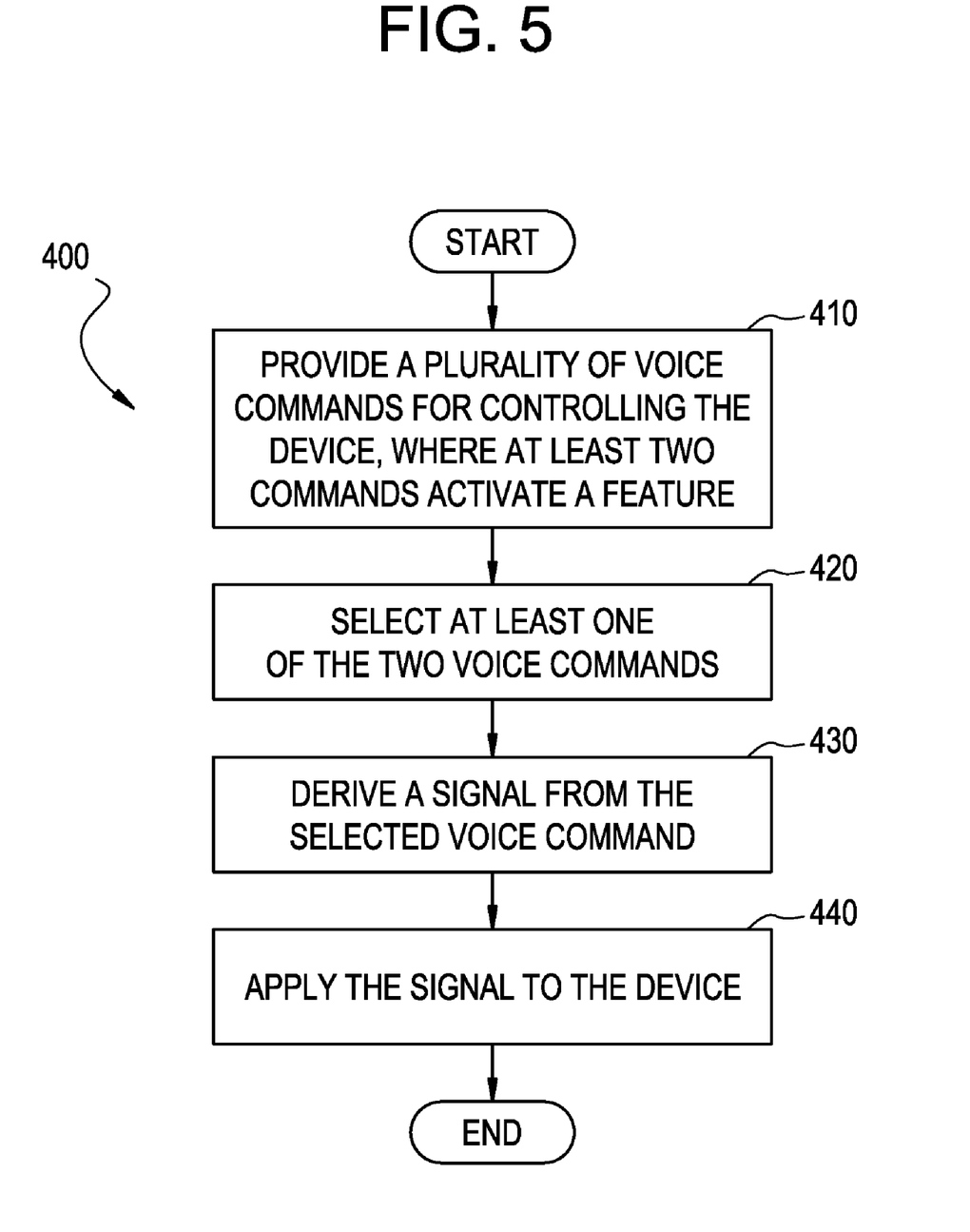
FIG. 5 illustrates a high level flow diagram depicting a method for controlling an ultrasound machine or device (similar to that illustrated in FIGS. 1 and 2) using natural voice control in accordance with certain embodiments of the present invention.
Figure 6:
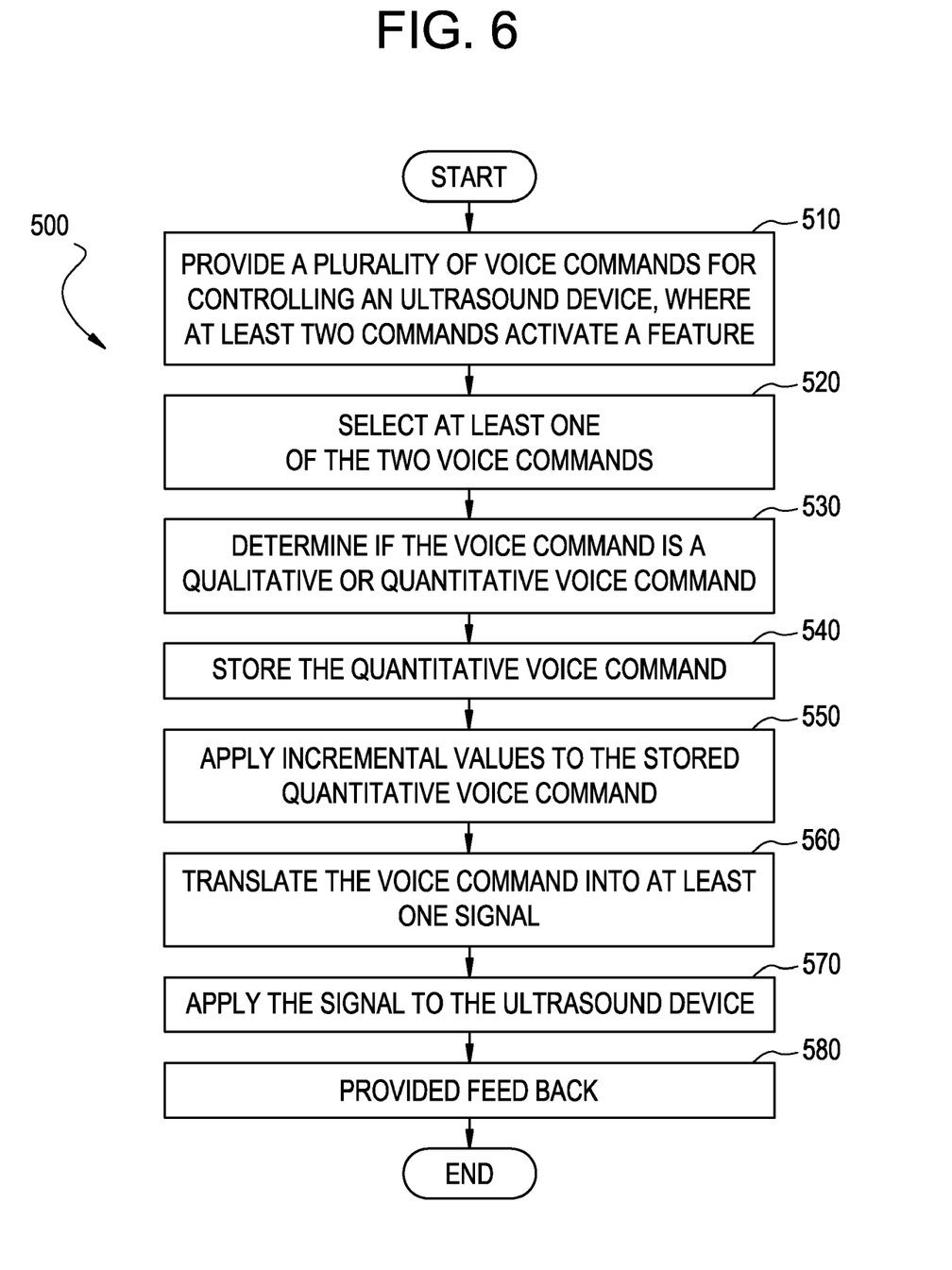
FIG. 6 illustrates a detailed flow diagram depicting a method for controlling an ultrasound machine or device (similar to that illustrated in FIGS. 1 and 2) using natural voice control in accordance with certain embodiments of the present invention.

If is further contemplated that, during normal usage, the system may display a volume meter. This verifies that the system is listening to the user. The volume meter may comprise a bar (horizontal or vertical), a microphone with "sound signals" extruding from it, a logo that changes color, etc. FIGS. 5 and 6 depict flow charts illustrating embodiments of a methods of controlling a device (an ultrasound system or device for example). FIG. 5 depicts a high level flow chart illustrating a method, generally designated 400, of controlling a system or device similar to that provided previously. In the illustrated embodiment, method 400 comprises Step 410, providing a plurality of voice commands for controlling the system or device. In one embodiment, the plurality of voice commands comprise at least two different voice commands that activate a single feature of the device.

Method 400 further comprises Step 420, selecting at least one of the at least two different voice commands. Step 430 comprises deriving a signal from the selected voice command. Step 440 comprises applying the signal to the device or system.

FIG. 6 depicts a detailed flow chart illustrating a method, generally designated 500, for controlling a system or device similar to that provided previously. In the illustrated embodiment, method 500 comprises Step 510, providing a plurality of voice commands for controlling an ultrasound device. In one embodiment, the plurality of voice commands comprise at least two different voice commands that activate a single feature of the device.

Method 500 further comprises Step 520, selecting at least one of the at least two different voice commands. Step 530 comprises determining if the voice command is a qualitative or quantitative voice command. If the voice command is a quantitative voice command, in at least one embodiment, method 500 comprises Step 540, storing the quantitative voice command, and Step 550, applying one or more incremental values to the stored quantitative voice command.

Method 500 further comprises Step 560, translating the voice command into at least one signal. Step 570 comprises applying the signal to the ultrasound device. Step 580 comprises providing feedback, to the user for example.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A system for voice control of a medical imaging device, the system including:
a medical imaging device including a plurality of features;
a voice command input adapted to receive a verbal input; and
a control processor adapted to control at least one of the plurality of features based at least in part on a qualitative command, a quantitative command, and a default direction, wherein the qualitative command and the quantitative command are based at least in part on the verbal input, and wherein the qualitative command is associated with the at least one of the plurality of features, and wherein the quantitative command represents a numeric value.

2. The system of claim 1, wherein the medical imaging device includes an ultrasound system.

3. The system of claim 1, wherein the voice command input includes a microphone.

4. The system of claim 1, wherein the voice command input is wireless.

5. The system of claim 1, wherein the verbal input is received from a user.

6. The system of claim 1, further including a recognition engine adapted to processes the verbal input to determine at least one of the qualitative and quantitative commands.

7. The system of claim 6, wherein the recognition engine is in communication with the voice command input and the control processor.

8. The system of claim 6, wherein the recognition engine is adapted to process the verbal input based at least in part on a command grammar, wherein the command grammar includes a plurality of commands.

9. The system of claim 8, wherein each command in the plurality of commands is associated with a group, and wherein the recognition engine is adapted to process the verbal input based at least in part a selected group of commands in the command grammar.

10. The system of claim 1, wherein the numeric value relates to an adjustment of one of the plurality of features.

11. A method for voice control of a medical imaging device, the method including:
receiving a verbal input through a voice command in put;
controlling a feature of a medical imaging device with a control processor based at least in part on a qualitative command, a quantitative command, and a default direction, wherein the qualitative command and the quantitative command are based at least in part on the verbal input, and wherein the qualitative command is associated with the feature, and wherein the quantitative command represents a numeric value.

12. The method of claim 11, wherein the medical imaging device includes an ultrasound system.

13. The method of claim 11, further including processing the verbal input to determine at least one of the qualitative and quantitative commands.

14. The method of claim 13, wherein the verbal input is processed based at least in part on a command grammar, wherein the command grammar includes a plurality of commands.

15. The method of claim 14, wherein each command in the plurality of commands is associated with a group, and wherein the verbal input is processed based at least in part a selected group of commands in the command grammar.

16. The method of claim 13, wherein the verbal input is processed by a recognition engine.

17. The method of claim 11, wherein the numeric value relates to an adjustment of one of the plurality of features.

18. A method for voice control of a medical imaging device, the method including:

controlling a feature of a medical imaging device with a control processor based at least in part on a qualitative command, a quantitative command, and a default direction, wherein the qualitative command and the quantitative command are based at least in part on a verbal input received through a voice command input, and wherein the qualitative command is associated with an adjustable feature of the medical imaging device, and wherein the quantitative command represents a numeric value relates to the adjustable feature of the medical imaging device.

* * * * *